United States Patent [19]
Paciej et al.

[11] Patent Number: 5,036,707
[45] Date of Patent: Aug. 6, 1991

[54] ULTRASONIC TESTING APPARATUS AND METHOD FOR RAPIDLY INSPECTING A LARGE NUMBER OF GAS CYLINDERS OF SIMILAR DESIGN FOR INTERNAL NECK-SHOULDER DEFECTS

[75] Inventors: Richard C. Paciej, Lansdale, Pa.; Robert E. Lewis, Westfield, N.J.

[73] Assignee: The BOC Group, Inc., New Providence, N.J.

[21] Appl. No.: 491,891

[22] Filed: Mar. 12, 1990

[51] Int. Cl.$^5$ .............................................. G01N 9/24
[52] U.S. Cl. ...................................... 73/637; 73/633
[58] Field of Search ............... 73/620, 622, 627, 633, 73/634, 637, 638, 640

[56] References Cited

U.S. PATENT DOCUMENTS

| | | | |
|---|---|---|---|
| 3,934,457 | 1/1976 | Clark et al. | 73/637 |
| 4,502,331 | 3/1985 | Singh et al. | 73/627 |
| 4,577,505 | 3/1986 | Jestrich et al. | 73/629 |

OTHER PUBLICATIONS

Combustion Engineering, "AMDATA Scanning Systems", 1988.

Primary Examiner—Hezron E. Williams
Assistant Examiner—Louis M. Arana
Attorney, Agent, or Firm—Robert I. Pearlman; David M. Rosenblum

[57] ABSTRACT

The present invention provides an apparatus and method for ultrasonically testing the internal neck-shoulder region of a large number of gas cylinders for radially oriented defects. The apparatus and method includes housing an ultrasonic transducer within a shoe in a predetermined orientation wherein the transducer is wedged at a wedge angle so that ultrasonic pulses travel directly through the shoulder region to the top and bottom of the internal neck-shoulder region and is also outwardly skewed within the shoe at a skew angle such that the radially oriented defects reflect the ultrasonic pulses and produce return echoes. An automated scanner moves the shoe and therefore, the transducer in a predetermined pattern such that the entire internal neck-shoulder region of the gas cylinder is scanned. The scanner is supported by a stand that allows the automated scanner to be rapidly set up on the gas cylinders being tested. A processor activates the transducer to produce ultrasonic pulses, controls the automated scanner and responds to the return echoes for indicating the presence of the radial defects that require the removal of a particular one of the gas cylinders from service.

10 Claims, 5 Drawing Sheets

ULTRASONIC TESTING APPARATUS AND METHOD FOR RAPIDLY INSPECTING A LARGE NUMBER OF GAS CYLINDERS OF SIMILAR DESIGN FOR INTERNAL NECK-SHOULDER DEFECTS

BACKGROUND OF THE INVENTION

The present invention relates to an ultrasonic testing apparatus and method for rapidly inspecting a large number of gas cylinders of similar design for defects located in the internal neck-shoulder region. More particularly, the apparatus and method of the present invention allows for the rapid production of ultrasonic images of the internal neck-shoulder region of the gas cylinders in order to uncover radially oriented defects such as cracks or folds. Such defects, if undetected, can result in leakage of the contents of the gas cylinder. This may be particularly dangerous in case a toxic substance is stored in the gas cylinder.

In the prior art, the neck-shoulder region of a gas cylinder is inspected by removing the valve from the head of the gas cylinder and then inserting a dental mirror into the head opening of the gas cylinder. A light is then directed down the head opening and the mirror is maneuvered for visual inspection of the internal neck-shoulder region of the gas cylinder for defects. A major problem with this technique is that it is extremely time consuming and therefore, not practical if large numbers of cylinder are to be inspected. Moreover, cracks growing from folds may be easily overlooked. In some cases, small harmless folds may exist in the shoulder, but it is often difficult to judge how deep they may be and these cylinders may be unnecessarily rejected. Thus, neck-shoulder region defects in gas cylinders are either missed; or when found, can result in a unnecessary withdrawal of the gas cylinder from service.

The prior art has provided ultrasonic testing techniques to inspect welds and surfaces, such as the inner and outer surfaces of a pipe or a plate, for cracks, voids and other defects. In an ultrasonic testing technique referred to as the angle-beam technique, an ultrasonic transducer is mounted within a transducer shoe at an oblique vertical angle, called a wedge angle, to insure that the ultrasonic pulse emitted by the transducer skips between the opposed surfaces of the pipe or plate at points called nodes and thereby encounters the defects at an angle to produce return echoes. It should be noted that return echoes are produced at gas-metal interfaces, for instance, at the air gap located between the internal surfaces of a crack. If a pulse encounters a crack in a direction parallel to the plane of the crack, there is simply not enough area of interface to produce a return echo. The skip distance, that is the distance between two nodes, is determined by calculation, measurement by a separate transducer, or by an angle beam test block, in order to thereby determine the area in which the transducer is to be moved to scan an area of interest. Typically, the area of interest is scanned by moving the shoe in a zig-zag path, parallel to the area of interest, between one-half and one full skip distance from the area of interest. Additionally, the shoe may be positioned at a fixed point, typically one full skip distance or less from the area of interest and horizontally swiveled or skewed from side to side to determine the depth of the defect.

The above-mentioned angle-beam technique may be performed by a skilled technician manually positioning the shoe. A processor is provided to activate the transducer to emit ultrasonic pulses and to respond to return echoes, produced by the reflection of the ultrasonic pulses, by graphically displaying the amplitude of the return echoes against time on an oscilloscope. The skilled technician then interprets the graphical display on the scope to determine the size and the position of defects. The prior art has also provided automated testing apparatus that automatically scans the article being tested and automatically processes the ultrasonic pulses and return echoes to produce interpretive displays.

The automated scanning apparatus of the prior art moves the shoe and thus, the transducer through a predetermined path to scan the area of interest. Such scanning apparatus may include a wheeled vehicle having magnetic wheels that ride on a steel, band-like track that is attached to the article being tested; for instance, the circumference of a pipe. The shoe housing the transducer is connected to the wheeled vehicle by means of an arm that can retract and extend the shoe in directions toward and away from the wheeled vehicle to scan an area of interest as the vehicle travels around the track.

The interpretive display produced by such automated prior art testing apparatus may utilize three display modes to graphically display the defects, namely, an A-scan, a B-scan and a C-scan. The A-scan displays a plot of return echo signal amplitude versus time. Defect size may be estimated by comparing the return echo signal amplitude with that produced by a flaw of known size and shape. The B-scan displays a plot of time versus the position of the transducer. Return echo signal amplitude is indicated by preprogrammed brightness or color indications on the plot. Such plot is used to indicate the position and the orientation of flaws and defects in the article being tested. Lastly, the C-scan display is a plot of a plan or view of the article being tested with flaws and defects superimposed over such plan view. Automated processing systems that display C-scan plots have electronic depth gate circuitry to limit the number of echo signals that are processed within a preselected range of signal delay times. This allows a region of the article, parallel to the surface being scanned, to be selected for display.

Angle beam ultrasonic testing techniques, either manual or automatic, have not heretofor been utilized in the testing of the neck-shoulder region of gas cylinder heads for cracks and folds because the head of the gas cylinder is not longitudinally symmetrical. Here it is relevant to point out in the performance of any ultrasonic inspection technique, the shoe must be positioned flush against a sound conducting couplant coating the outer surface of the article to be tested. If a gap exists between the couplant and the shoe, the ultrasonic pulse will not enter the article. If one were to conventionally test the internal neck-shoulder region of the cylinder head for defects by the angle beam technique, the change of surface slope at the juncture of the head and shoulder of the cylinder would make the requisite contact between the shoe and the outer surface impossible. Moreover, since angle-beam techniques contemplate moving the shoe in a predetermined pattern in a region near the defect, such change and surface slope would prevent the required movement of the shoe. It should be mentioned that one skilled in the art would not be led to scan the material neck-shoulder region of the gas cylinder from the shoulder region because the longitudinal asymmetry of the gas cylinder head causes the skip distance to vary with the thickness and change in surface of the cylinder head; and therefore, there has been no known method to compute the wedge angle. Another reason as to why one would not be led to position the shoe on the shoulder region of the gas cylinder is that radially oriented defects would be scanned edge wise, parallel to the extent of the defects, and therefore not produce a return echo.

If the above-mentioned problems associated with ultrasonically scanning the internal neck-shoulder region of a gas cylinder were solved, a large number of gas cylinders could be rapidly inspected for neck-shoulder defects. However, a skilled technician would be required to perform the test and interpret the results. As will be discussed, automated ultrasonic testing apparatus is used in the present invention to even more rapidly inspect large numbers of gas cylinders for neck-shoulder defects; and further to eliminate the need for a skilled technician to perform the inspection. However, such automated ultrasonic testing apparatus must be set up on each similar gas cylinder in a prescribed location and orientation. The "Set-up" of such automated apparatus is time consuming in and of itself and, thus such apparatus does not readily lend itself to the inspection of a large number of gas cylinder for neck-shoulder defects.

As will be described in more detail hereinbelow the present invention provides an ultrasonic testing apparatus and method for testing the neck-shoulder region of a gas cylinder for defects. The method and apparatus of the present invention lends itself for use with automated scanning apparatus with elimination of set-up time delay so that the ultrasonic test may be performed on a large number of gas cylinders without any special exercise of skill or training required on the part of the person performing the test.

SUMMARY OF THE INVENTION

The present invention provides an apparatus and method for ultrasonically inspecting the internal neck-shoulder region of a large number of gas cylinders for radially oriented defects. The apparatus and method utilizes an ultrasonic transducer positioned in a predetermined orientation wherein the transducer is wedged at a wedge angle determined such that ultrasonic pulses emitted by the transducer travel directly from the outer surface of the cylinder shoulders to the top and bottom of the internal neck-shoulder regions of the gas cylinders when the shoe is respectively positioned at the top and bottom of the shoulder. Therefore, unlike conventional angle beam techniques, the wedge angle of the present invention is only being utilized to insure that the ultrasonic pulses reach the intended remote surface to be scanned and not also to resolve defects by encountering them at an angle. Moreover, in the present invention. quite unlike conventional angle beam techniques, defects are resolved by outwardly skewing the transducer at a skew angle determined such that the radially oriented defects reflect the ultrasonic pulses and produce return echoes when the shoe is rotated around the shoulder of each of the gas cylinders. Retaining means are provided for retaining the transducer in the predetermined orientation and for contacting the shoulders of the gas cylinders so that the ultrasonic pulses enter the shoulders when covered with a sound conductive couplant. Automated scanning means are provided for moving the retaining means and therefore, the transducer in a predetermined pattern, from the top to the bottom and around the shoulder of each of the gas cylinders such that the entire internal neck-shoulder region thereof is scanned. Stand means are connected to the scanning means and are adapted to receive each of the gas cylinders to automatically position the automatic scanning means so that the automated scanning means may uniformly move the retaining means in the predetermined scan pattern on each of the gas cylinders upon reception. Lastly, processing means control the scan position of the scanning means, activate the transducer to emit the ultrasonic pulses, and respond to the return echoes for indicating the presence of the radially oriented defects.

In accordance with the method of the present invention, the wedge and skew angles are first determined. Thereafter, the retaining means are fabricated for retaining the transducer in the predetermined position in which the wedge and skew angles are preset. The automated scanning means are then connected to the stand means; the shoulders of each of the gas cylinders is coated with the sound conducting couplant, and each of the gas cylinders is received within the stand means. The scan pattern of the scanning means is controlled and the transducer is activated by the processing means. Since the wedge and skew angles are preset and the stand means automatically position the automated scanning means, a skilled technician is not required to perform the inspection nor set up the automated scanning means. Moreover, the automatic set up of the automated scanning means by the stand means reduces the set up time to a minimum.

BRIEF DESCRIPTION OF THE DRAWINGS

While the specification concludes with claims particularly pointing out the subject matter that Applicants' regard as their invention, it is believed that the invention will be better understood from the following description taken in conjunction with the accompanying drawings in which:

DETAILED DESCRIPTION

Figure 1:
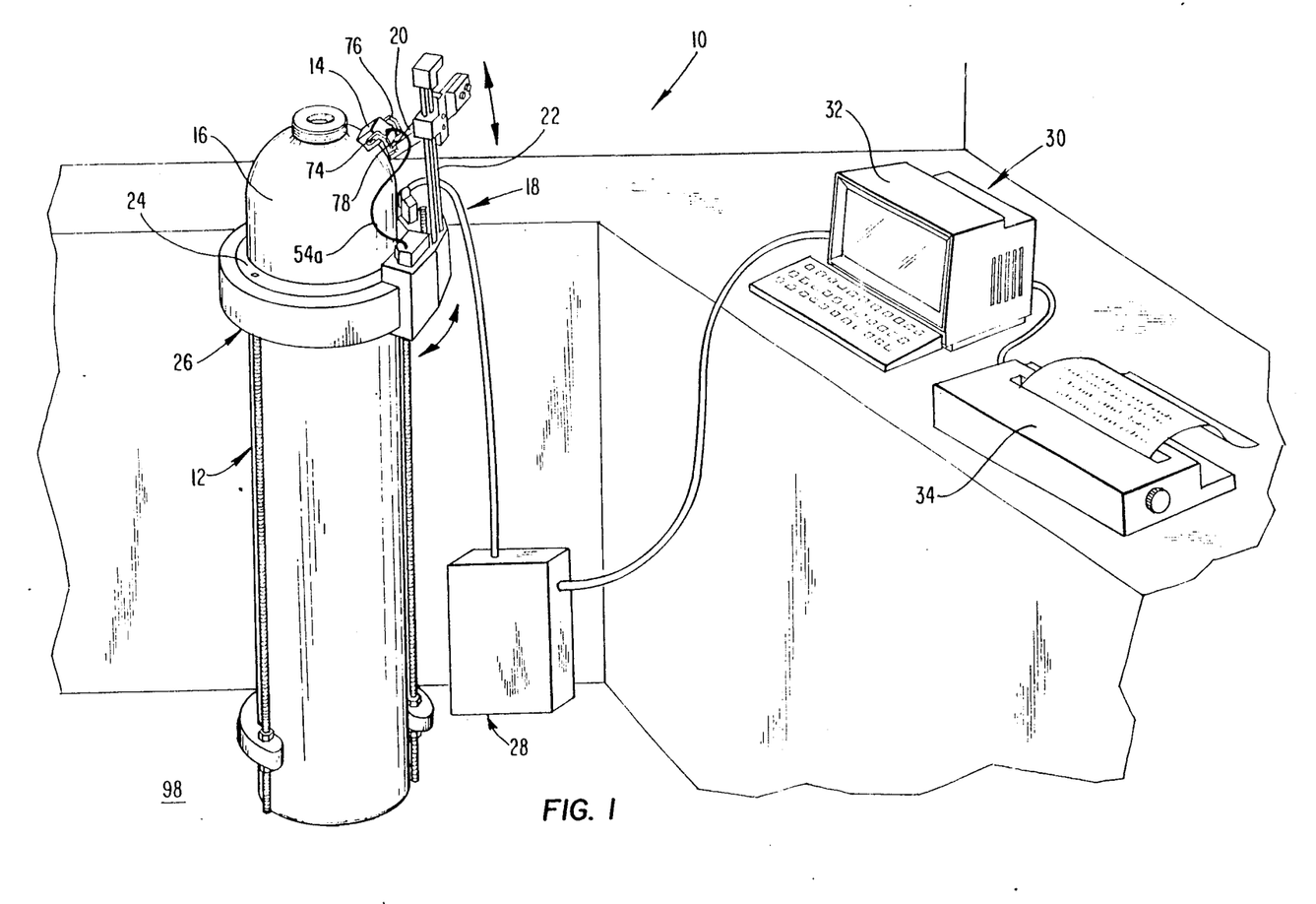
FIG. 1 is a perspective view of an ultrasonic inspection apparatus in accordance with the present invention.

With reference to FIG. 1, an ultrasonic inspection apparatus 10 in accordance with the present invention is illustrated performing a test on a gas cylinder 12. Ultrasonic inspection apparatus 10 includes a shoe 14 illustrated as riding on the shoulder 16 of gas cylinder 12 and an automated scanner 18. Shoe 14 is connected by a shoe holder 20 to an extensible arm 22 of scanner 18. Scanner 18, by provision of magnetic wheels, rotates around the circumference of cylinder 12 by means of a track 24. A stand 26 supports track 24 and thus, scanner 18 at a predetermined height, with track 24 in a level orientation and cylinder 12 centered within track 24.

As will be discussed in greater detail, arm 22 retracts to move shoe 14 and therefore, the transducer housed within shoe 14, in a downward direction along shoulder 16 of gas cylinder 12. Such retraction is accomplished in steps. In each of the steps, scanner 18, which is an automated wheeled vehicle, rotates about track 24 one complete turn to thereby rotate shoe 14 and its transducer 360° around shoulder 16. This predetermined motion moves transducer 14 to produce an ultrasonic scan of the internal neck-shoulder head region of cylinder 12. Movement of scanner 18 is controlled by a controller 28. A computer 30 is provided to activate the transducer to produce ultrasonic pulses and to respond to the return echoes produced by reflections of the ultrasonic pulses. In computer 30, the time differentials between the pulses and the return echoes are computed to produce a data point for each vertical position of transducer 14 and each horizontal position of scanner 18 on track 24. The data points are processed by computer 30 and may be output to a color monitor 32 or to a printer 34. The computer also allows the presetting of a variety of parameters that are used in controlling scanner 18 and the processing of data points derived from the ultrasonic pulses and the return echoes. Scanner 18, control 28, and computer 30 are preferably readily obtained components manufactured by AMDATA, Inc. of 775 Montaque Expressway, Milpitas, Calif. 95035 as components of its Intraspect/PC Series of Ultrasonic Testing and Imaging systems.

Figure 2:
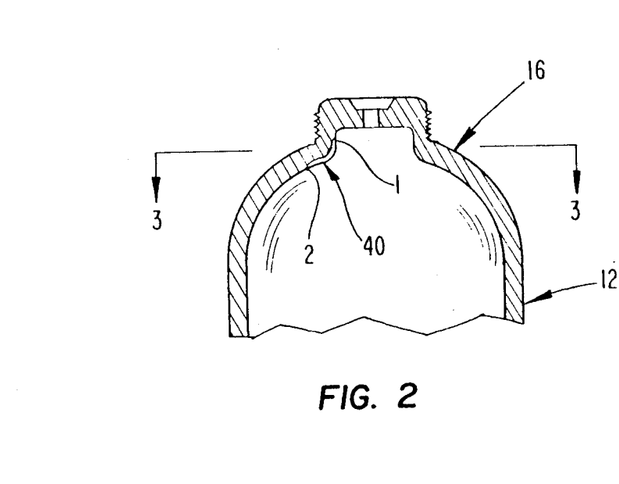
FIG. 2 is a fragmentary cross-sectional view of the gas cylinder being inspected in FIG. 1.
Figure 3:
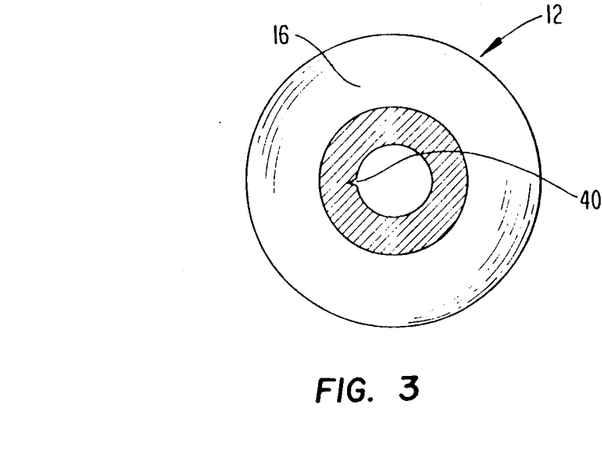
FIG. 3 is a cross-sectional view of FIG. 1 taken along line 3—3 of FIG. 2.

Referring to FIGS. 2 and 3, a crack 40 is illustrated in the neck-shoulder region of cylinder 12 defined between reference numerals 1 and 2. The problem with ultrasonically imaging the neck-shoulder region of a gas cylinder is that it is nonsymmetrical in the length-wise direction; and the shoe, housing the transducer, must be positioned against a sound conducting couplant covering the side of the cylinder in order to perform an ultrasonic inspection. Since shoulder 16 spherically slopes toward the neck of cylinder 12, which in turn rises vertically from shoulder 16, there is no location at the level of crack 40 on which a shoe may be positioned. The present invention solves this problem by allowing the shoe to be positioned on the next regular surface, closest to the neck-shoulder region, namely shoulder 16. However, since ultrasonic pulses would tend to image the shoulder 16 alone, the present invention provides a shoe in which the transducer is oriented to scan the internal neck-shoulder region formed in the region designated between reference numerals 1 and 2.

Figure 4:
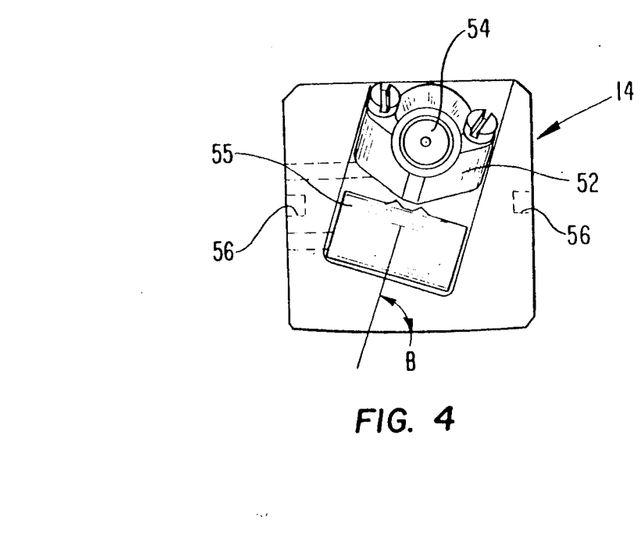
FIG. 4 is a top plan view of a transducer shoe in accordance with the present invention.
Figure 5:
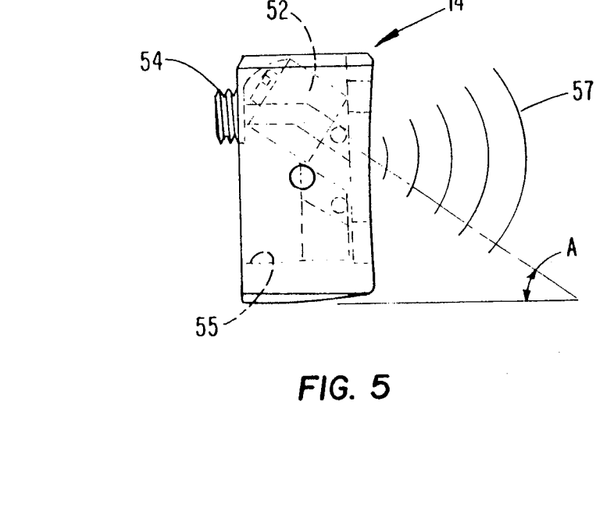
FIG. 5 is an elevational view of the transducer shoe of FIG. 4.

With reference to FIGS. 4 and 5, shoe 14 is of rectangular, block-like configuration and houses a transducer 52. Transducer 52 is connected at threaded fitting 54 by an electrical cable 54 to scanner 18. Transducer 52 is wedged at an angle "A" so that when shoe 14 is positioned at the top of shoulder 16, ultrasonic pulses 57 emitted by transducer 52 are directed to the top of internal neck-shoulder region designated by reference numeral 1; and when shoe 14 is positioned at the bottom of shoulder 16, the ultrasonic pulses are directed to the bottom of internal neck-shoulder region designated by reference numeral 2. In order to resolve the defects, transducer 52 is outwardly skewed at a skew angle "B".

This outward skew angle ensures that ultrasonic pulses will scan possible defects, such as crack 40 at an angle to produce return echoes from the pulses. As illustrated, transducer 52 is set within an elongated cavity 55 at wedge angle "A"; the cavity angled to one of the sides of shoe 14 to produce the skew angle "B". Additionally, side bores 56 are provided to pivotably attach transducer 52 by way of pins to the forked members of transducer holders that will be described hereinafter.

In the case of an aluminum alloy cylinder head, such as a LUXFER Size N152, the wedge angle "A" is about 45° and the skew angle "B" is about 15°. The wedge and skew angles are dependent upon a variety of factors including the type of transducer used. In this regard, the transducer is preferably a 0.635 cm; 2.25 MHz transducer to ensure a narrow pulse width and the passage of the pulses directly to the neck-shoulder region. Cylinder material and the physical configuration of the cylinder will also effect the wedge and skew angles and hence, wedge and skew angles must be determined for the particular gas cylinder to be tested.

The wedge and skew angles are determined by the use of the following apparatus and methodology. Turning first to the wedge angle, a calibration cylinder head is prepared by sawing off the head of a known cylinder having neck and shoulder regions similar to that of the cylinders to be tested; and then, medially dividing the sawed-off head along the cylinder's central axis. A number of test transducers are fabricated with a 0° skew angle and a variety of wedge angles which may vary in a range between about 0° and 90°. In determining the wedge angle "A" of transducer 52, three test transducers were fabricated having wedge angles of about 45°, 65° and 75°. An ultrasonic absorption source is then placed at the top of the internal neck-shoulder region at the same location as reference numeral 1 and at the bottom of the neck-shoulder region at the same location as reference numeral 2. In the fabrication of shoe 14 and transducer 52, the absorption source was applicant's finger. Each of the test shoes are then positioned opposite to the absorption source at the top and bottom of the shoulder, until it is determined that the absorption of the pulses emitted by the transducer is at a maximum. In the case of the aforementioned LUXFER aluminum cylinder head, the shoe incorporating a transducer with a wedge angle of 45° was found to have the maximum absorption and therefore, 45° was selected as the wedge angle.

Figure 6:
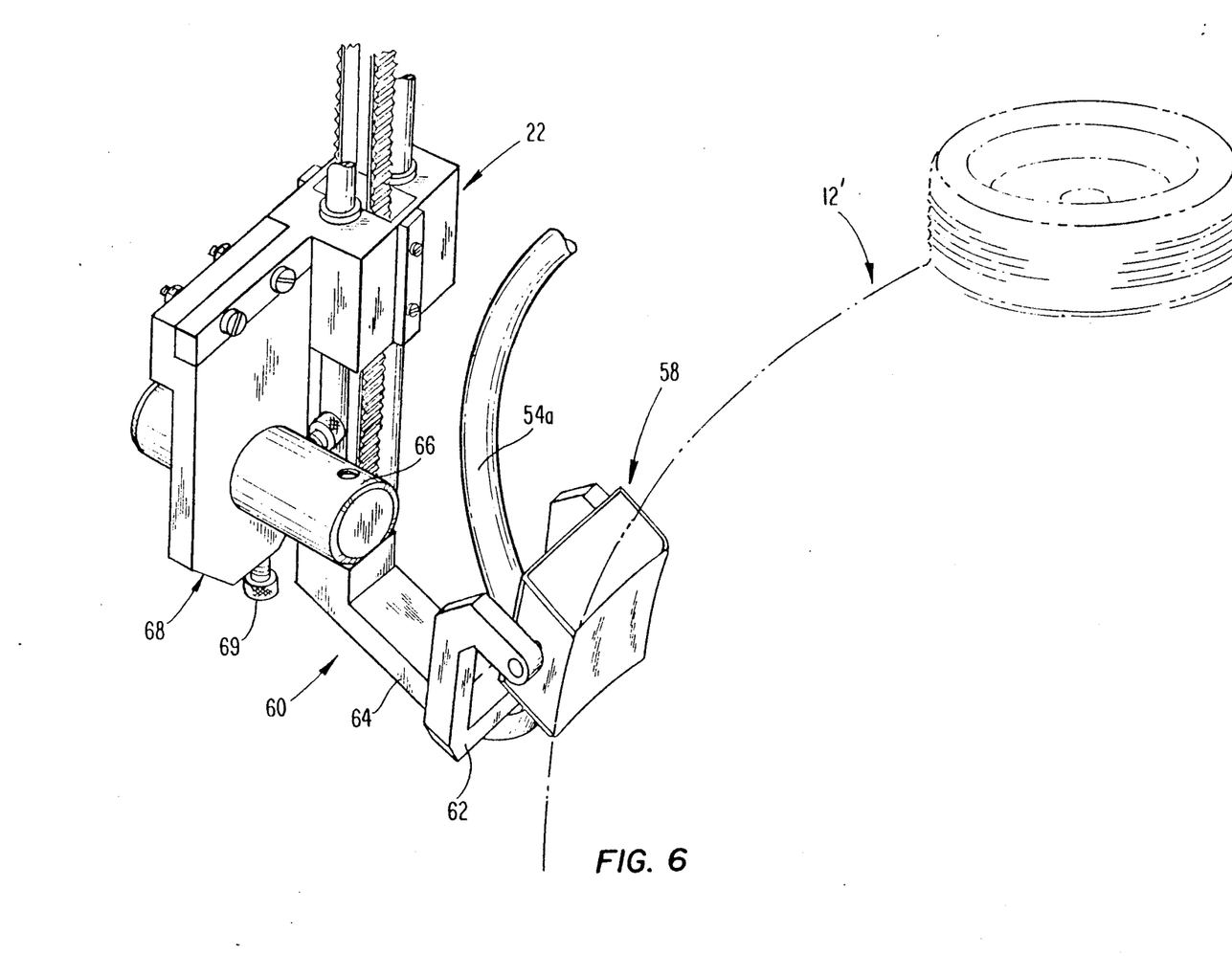
FIG. 6 is a perspective view of a test shoe holder in accordance with the present invention that is used as a tool for determining the required skew angle of a transducer.

With reference to FIG. 6, in order to determine the skew angle, another calibration cylinder head 12' is fabricated with an EDM (Electro-Discharge Method) notch in the neck-shoulder region. The EDM notch should have a length of that of the neck-shoulder region (between reference numerals 1 and 2). Calibration cylinder head 12' may be formed by sawing-off the head of a gas cylinder having neck and shoulder regions similar to that of the cylinders to be tested. A transducer shoe and transducer, designated by reference numeral 58, having the selected wedge angle and a 0° skew angle is mounted in a test transducer holder 60. Transducer holder 60 has a forked member 62 pivotably attached to an arm 64. Arm member 64 is attached to a cylindrical member 66 that passes through a bore of a bracket member 68 which is in turn attached to arm 22 of scanner 18. Forked member 62 is free to pivot about an axis normal to the shoulder of calibration gas cylinder head 12' while cylindrical member 66 is free to rotate within bracket member 68 until locked in position by a set screw 69. When cylindrical member 66 is rotated, for instance in a clockwise direction, forked member 62, along with shoe 58, tends to rotate on the surface of the shoulder of the other calibration cylinder head in a counter clockwise direction and vice-versa. Although not illustrated, the end of cylindrical member 66 projecting from bracket member 68 is preferably marked, along with the adjacent surface of bracket member 68, to indicate the degrees of rotation of forked member 62 and shoe/transducer 58. Shoe/transducer 58 is rotated past the calibration notch at a variety of incremental, outward (i.e. clockwise) angular settings until a maximum return signal amplitude is produced by the calibration notch. In case of the aforementioned LUXFER aluminum alloy cylinder, the angle of maximum return or the determined skew angle was found to be about 15°.

Figure 7:
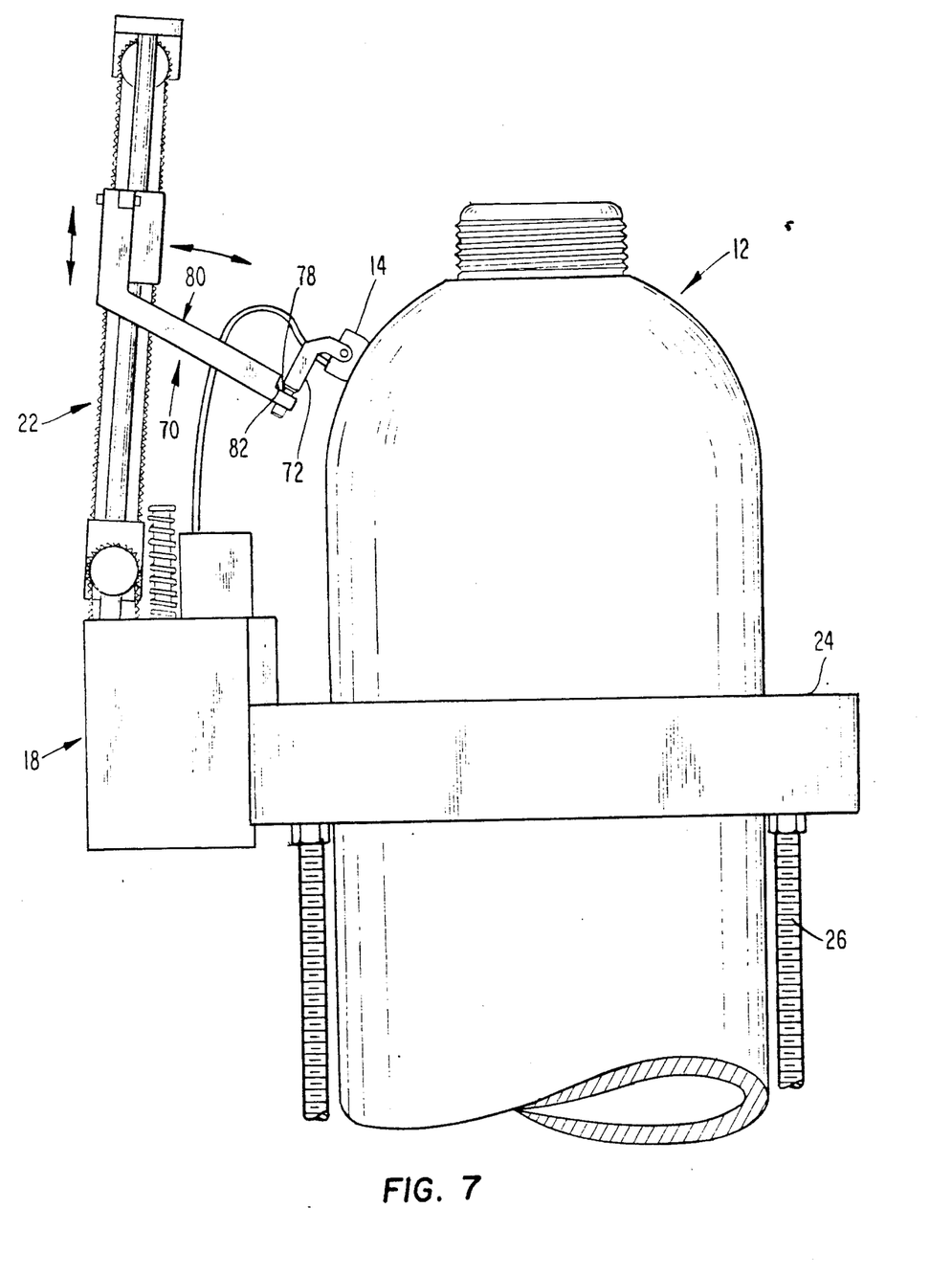
FIG. 7 is a fragmentary elevational view of FIG. 1.

With reference to FIG. 7, during a large scale testing operation of a multitude of cylinders, such as cylinder 12, a shoe holder 70 is utilized to hold shoe 14. Shoe holder 70 has a forked member 72 at one end. Shoe 14 is pivotably connected to a pair of fork elements 74 and 76 of forked number 72 so as to be able to swing in the vertical direction. A crown element 78 connecting the fork elements 74 and 76 of forked member 72 is in turn pivotably connected to an elongated member 80 of shoe holder 70 at a step or shoulder 82. Step 82 allows some rotational movement of forked member 70 and shoe 14 in order to prevent the shoe from snagging against discontinuities such as raised lettering found in the shoulder of some cylinder heads. In this regard, the preferred allowed rotational movement allowed is about six degrees (three degrees in either direction).

A shoe incorporating a transducer in a predetermined position in which the wedge and skew angles are preset allow for the rapid testing of many similar cylinders. The addition of attaching the shoe to automated scanning devices, such as the AMDATA device, described above, further reduces the time expended in the testing of a variety of similar cylinders. However, as may be appreciated, scanner 18 and track 24 must be set up so that cylinder 12 is centered within track 24, track 24 is in a level orientation and is at a predetermined position on each of the cylinders. The stand 26 provided in the present invention allows for a rapid setup time of scanner 18 and track 24 by being operable to receive the gas cylinders so that the scanning means are automatically positioned to uniformly scan each of the cylinders upon reception.

Figure 8:
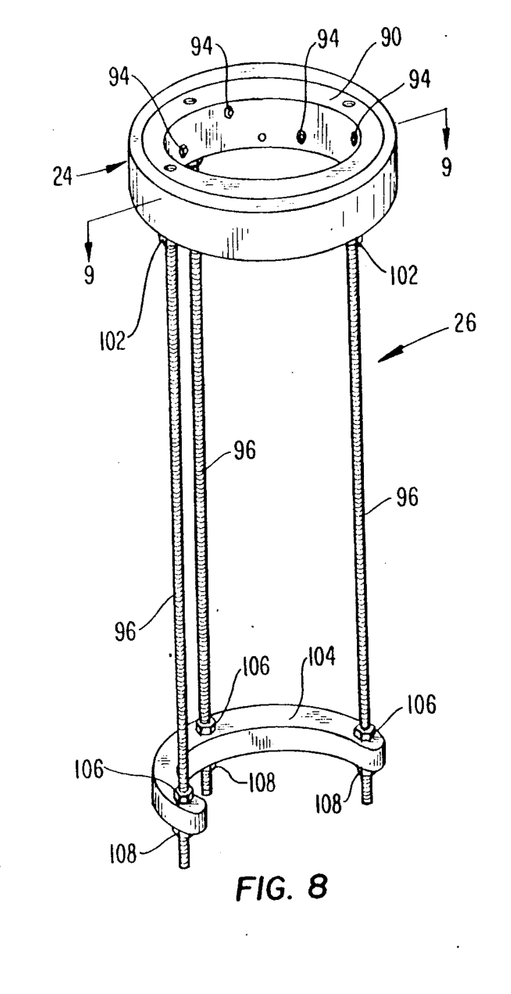
FIG. 8 is a perspective view of a stand in accordance with the present invention that is used to support a hoop-like track on which an automated scanner rides.
Figure 9:
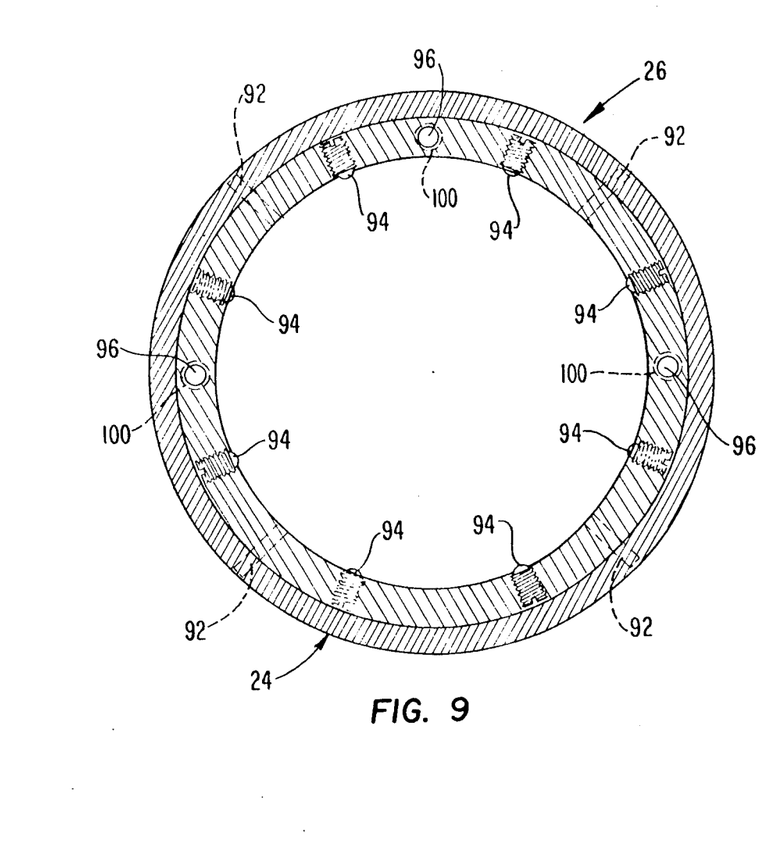
FIG. 9 is a cross-sectional view of FIG. 8 taken along line 9—9 of FIG. 8.

Turning now to FIGS. 8 and 9, stand 26 is provided with an annular element 90 having a set of at least three; but preferably four radially projecting studs 92. Track 24 is provided in two sections having bores to receive studs 92 and thereby concentrically attach track 24 to annular member 90. Annular member 90 is also provided with a set of eight, circumferentially spaced, inwardly directed, spring loaded ball plungers 94 to engage the side of cylinder 12. When annular member 90 and track 24 is either lowered onto cylinder 12 or cylinder 12 is upwardly nosed through annular member 90, the balls of the spring loaded plungers 94 contact the side surface of cylinder 12 to center cylinder 12 within annular member 90 and therefore, track 24.

Stand 26 is also provided with at least one, but preferably three legs 96, that depend from annular member 90 to contact surface 98 on which cylinder 12 is supported and thereby preadjust the height of annular member 90 and therefore, track 24. Preferably, the top end of legs 96 are threaded to be threadably received within bores 100 of annular member 90 so that some degree of height adjustment of annular member 90 and track 24 is permitted. Such height adjustment is locked in place by provision of three lock nuts 102 also threaded onto the top ends of legs 96.

In order to ensure that track 24 is perfectly level in all directions, an arcuate member 104 is provided with a set of three bores to receive the lower ends of legs 96. The lower ends of legs 96 are threaded to receive lock nuts 106 and 108 on the top and bottom of arcuate member 104 for locking arcuate member 104 in place and for adjusting the height of arcuate member 104. Arcuate member 104 is configured to conform to the outer surface of cylinder 12 and to ensure that legs 96 are parallel to the central axis of cylinder 12.

The AMDATA Ultrasonic Image System is capable of producing A-scan, B-scan and C-scan interpretive displays on the computer 30 monitor or alternately by printer 34. However, prior to the performance of inspection runs, the AMDATA system is first calibrated by using the calibration cylinder head 12' that was previously used in determining the skew angle. In this regard, it has been determined that a defect having a depth of at least about 2.04 mm. in a LUXFER Size N152 gas cylinder is indicative that such cylinder should be withdrawn from service in case a toxic gas is stored within such cylinder. A defect having a depth of at least about 3.05 mm. is indicative of service removal of a LUXFER Size N152 gas cylinder when used for storing non-toxic substances. As will be discussed, the AMDATA system can be set to indicate the depth of a defect when calibrated with an EDM notch having the depth of such defect and further, is capable of displaying such defect depth indications so that only the minimum of training is required to interpret the display. Therefore, the EDM notch used in determining skew angles should have a depth of about 2.04 mm. or 3.05 mm; depending upon the toxicity of the gas stored, when testing a LUXFER Size N152 gas cylinder.

Prior to the actual calibration, the AMDATA system is set for ten scans, taking 2.02 mm, steps in the y-direction. The equipment is also set for a 45° angle beam and a 15° clockwise skew. The electronic depth gate circuitry is then set at 30 microsecond delay and the gain is adjusted at about 80% of the amplitude of the emitted ultrasonic pulses. In the AMDATA equipment, this is accomplished by adjusting the gain to provide 90%±10% full scan height from the return signal amplitude produced by the EDM notch. The AMDATA equipment color codes the intensity of return echo signal strength to indicate the depth of defects. In practice, the AMDATA system is set to code return echo signals of between 80%-100% by magenta, between 50%-79% white and 0%-49% as black. Thus, after calibration, when a return echo signal amplitude is 80% or greater, as indicated by one or more magenta data points on the B- or C- scans, it is known that the defect has a depth equal to or greater than that of the EDM notch.

After calibration of the instrument, the cylinders to be tested are coated with a couplant to conduct the emitted pulses from the shoe into the shoulders of the cylinders. The couplant in the case of the aforementioned LUXFER Size N152 gas cylinder is preferably glycerol which must be wiped off after the test to prevent corrosion. As may be appreciated, the calibration cylinder heads, discussed above, are also coated with the glycerol couplant and wiped clean after their use in determining the wedge and skew angles and in calibration of the AMDATA system.

The AMDATA system is then zeroed in an x-y coordinate system at 0.0, 0.0 cm, and the scanner 18 is then reset to make four complete scans around each cylinder in 4.572 mm. overlapping steps and stop at coordinate 0.0, −13.716 mm. Stand 26 is then lowered onto each of the cylinders and A-, B-, and C- scans of the internal neck-shoulder regions are produced. In the event that a single magenta data point appears in either the B- or C- scans, the cylinder is then withdrawn from service. As may be appreciated, a simple protocol may be drawn up so that a technician with the minimum of training may perform the test.

While a preferred embodiment of the invention has been shown and described in detail, in will be readily understood and appreciated by those skilled in the art that numerous omissions, changes and additions may be made without parting from the spirit and scope of the invention.

We claim:

1. An apparatus for ultrasonically inspecting the internal neck-shoulder region of a large number of gas cylinders of similar design for radially oriented defects, said apparatus comprising:

an ultrasonic transducer positioned in a predetermined orientation wherein the transducer is wedged at a wedge angle such that ultrasonic pulses emitted by the transducer travel directly from the outer surface of the shoulders to the top and bottom of the internal neck-shoulder regions of the gas cylinders when the transducer is respectively positioned at the top and bottom of the shoulders, and wherein the transducer is outwardly skewed at a skew angle such that the radially oriented defects present a sufficient interfacial area to reflect the ultrasonic pulses and produce return echoes when the transducer is rotated around the shoulder of each of the gas cylinders;

retaining means for retaining the ultrasonic transducer in the predetermined orientation and for contacting the shoulders of the gas cylinders so that the ultrasonic pulses enter the shoulders when covered with a sound conducting couplant;

an automated scanner for moving the retaining means and therefore, the transducer in a predetermined scan pattern, from the top to the bottom and around the shoulder of each of the gas cylinders, so that the internal neck-shoulder region thereof is scanned, the automated scanner comprising, a hoop-like track sized to surround the gas cylinders and an automated wheeled vehicle mounted on the track and having an arm connected to the retaining means for moving the retaining means from the top to the bottom of the shoulders of the gas cylinders as the automated wheeled vehicle travels on the track, around the gas cylinders;

a stand comprising, an annular member concentrically connected to the track and having a set of at least three inwardly directed means adapted to releasably engage the sidewalls of the gas cylinders for centering the gas cylinders within the track, at least one elongated member depending, at right angles and at one end, from the annular member and sized such that the other of its ends contacts a surface on which the gas cylinders rest to insure the track is consistently supported at a predetermined height, and a horizontally oriented arcuate member, connected to the at least one elongated member, spaced from the other of the ends of the elongated member, and configured to conformingly contact the side of the gas cylinder such that at least one elongated member is parallel to the central axis of the gas cylinder and thus, the track is in a level orientation; and processing means controlling the scan pattern of the scanning means, actuating the transducer to emit ultrasonic pulses, and responsive to the return echoes produced by the radially oriented defects for indicating the presence of radially oriented defects.

2. The apparatus of claim 1, wherein the transducer retaining means comprises:

a shoe configured to ride on the shoulder of the gas cylinders and housing the ultrasonic transducer in the predetermined orientation; and shoe holding means for attaching the shoe to the automated scanning means.

3. The apparatus of claim 2, wherein:

the shoulders of the gas cylinders have raised discontinuities; and the shoe holding means comprises:

an elongated arm member connected, at one end, to the scanning means and having, at the other end, a shoulder; and a forked member including, a pair of forked elements pivotably connected to the shoe so that the shoe is free to pivot within the forked elements, and a crown element connecting the forked elements and pivotably connected to the other end of the arm member at the shoulder thereof so that the shoulder permits limited rotation of the forked member and therefore, the shoe, to prevent the shoe from snagging against the raised discontinuities.

4. The apparatus of claim 1, wherein:

each of the gas cylinders comprises a LUXFER Size N152 gas cylinder fabricated from aluminum alloy;

the transducer is a 0.635 cm., 2.25 MHz transducer;

the wedge angle is about 45.0 degrees; and the skew angle is about 15.0 degrees.

5. A method for ultrasonically inspecting the internal neck-shoulder regions of a large number of gas cylinders of similar design for radially oriented defects, said method comprising:

determining a wedge angle for an ultrasonic transducer such that ultrasonic pulses emitted by the ultrasonic transducer travel directly from the outer surface of the shoulder to the top and bottom of the internal neck-shoulder region of each of the gas cylinders when the transducer is respectively positioned at the top and bottom of the shoulder of each of the gas cylinders;

determining a skew angle for the transducer such that radially oriented defects present a sufficient interfacial area to reflect the ultrasonic pulses and produce return echoes when the transducer is rotated around the shoulder of each of the gas cylinders;

retaining the ultrasonic transducer in a predetermined orientation within a shoe wherein the transducer is wedged at the determined wedge angle and is outwardly skewed at the determined skew angle;

coating the shoulders of each of the gas cylinders with a sound conducting couplant;

moving the shoe and therefore, the transducer in a predetermined scan pattern, from the top to the bottom and around each of the shoulders of the gas cylinders, so that the internal neck-shoulder region thereof is scanned; and controlling the scan pattern and activating the transducer to emit ultrasonic pulses by processing means responsive to the return echoes for indicating the presence of the radially oriented defects.

6. The method of claim 5, wherein the wedge angle determination comprises:

fabricating a medially sectioned, calibration gas cylinder head having neck and shoulder regions identical to that of the gas cylinders to be tested;

fabricating a plurality of test shoes containing a plurality of test transducers angled at test wedge angles incrementally varying in a range of between about 0 and 90 degrees;

positioning each of the test shoes at the top and bottom of the shoulder of the calibration gas cylinder head;

positioning a sound adsorber at the top and bottom of the internal neck-shoulder region of the calibration gas cylinder head when each of the shoes is positioned at the top and bottom of the shoulder of the calibration calibration gas cylinder head;

activating the transducer to emit pulses by the processing means when the shoes are positioned at the top and bottom of the shoulders of calibration gas cylinder head; and selecting the wedge angle from the one test wedge angle of the one test shoe in which the processing means indicate that the emitted pulses are absorbed when the one test shoe is positioned at the top and bottom of the shoulder of the calibration gas cylinder head.

7. The method of claim 5, wherein the skew angle determination comprises:

fabricating a calibration gas cylinder head having neck and shoulder regions identical to the gas cylinders to be inspected;

inscribing a radially oriented calibration notch in the neck-shoulder region of the calibration gas cylinder head;

outwardly and incrementally rotating a test shoe, containing a transducer positioned at the determined wedge angle and at a skew angle of about 0.0 degrees, about an axis normal to the surface of the shoulder of the calibration gas cylinder head;

activating the transducer to emit pulses by the processing means;

rotating the test shoe around the shoulder of the calibration cylinder at each outer incremental rotation of the test shoe;

selecting the skew angle by noting the outer rotation of the test shoe when the processing means indicate a maximum return echo.

8. The method of claim 7, wherein:

the processing means indicate the size of a defect as a function of return echo amplitude and has means for adjusting the gain of the return echo amplitude; and wherein the method further comprises:

inscribing the calibration notch by electro-discharge machine method to have a length exceeding from the top to the bottom of the neck-shoulder region and a depth equal to the depth of radial oriented defects that require the removal of the gas cylinders from service;

rotating the test shoe past calibration notch; and calibrating the processing means by adjusting the gain of the return echo amplitude produced by the calibration notch to equal that of a fixed percentage of the emitted ultrasonic pulses so that the amplitude of return echoes produced by radially oriented defects above the fixed percentage indicate the removal of the gas cylinders from service.

9. The method of claim 8, wherein:

each of the gas cylinders comprise a LUXFER Size N152 gas cylinder fabricated from aluminum alloy and is used to contain a toxic gas;

the calibration notch is inscribed with a depth of about 2.04 mm.; and the processing means is adjusted so that the fixed percentage is about 80.0 percent.

10. The method of claim 8, wherein:

each of the gas cylinders comprise a LUXFER Size N152 gas cylinder fabricated from aluminum alloy and is used to contain a non-toxic gas;

the calibration notch is inscribed with a depth of about 3.05 mm.; and the processing means is adjusted so that the fixed percentage is about 80.0 percent.

* * * * *

UNITED STATES PATENT AND TRADEMARK OFFICE
CERTIFICATE OF CORRECTION

PATENT NO. : 5,036,707
DATED : August 6, 1991
INVENTOR(S) : Paciej et al.

It is certified that error appears in the above—identified patent and that said Letters Patent is hereby corrected as shown below:

Col. 12, line 18, delete the word "exceeding" and substitute therefor the word --extending--.

Signed and Sealed this

Twenty-eighth Day of September, 1993

Attest:

BRUCE LEHMAN

*Attesting Officer*  *Commissioner of Patents and Trademarks*